United States Patent [19]

Hlavacek

[11] Patent Number: 5,540,716
[45] Date of Patent: Jul. 30, 1996

[54] SURGICAL FASTENER

[75] Inventor: Robert A. Hlavacek, Navgetuck, Conn.

[73] Assignee: American Cyanamid Company, Wayne, N.J.

[21] Appl. No.: 346,327

[22] Filed: Nov. 29, 1994

Related U.S. Application Data

[63] Continuation of Ser. No. 107,880, Aug. 17, 1993, abandoned, which is a continuation of Ser. No. 868,155, Apr. 14, 1992, Pat. No. 5,236,440.

[51] Int. Cl.$^6$ .................................... A61B 17/00
[52] U.S. Cl. .................... 606/219; 606/213; 606/216; 227/902
[58] Field of Search .................... 606/213, 216, 606/219; 227/902

[56]        References Cited

U.S. PATENT DOCUMENTS

| | | | |
|---|---|---|---|
| 4,337,774 | 7/1982 | Perlin | 606/158 |
| 4,428,376 | 1/1984 | Mericle. | |
| 4,835,824 | 6/1989 | Darham | 606/157 |
| 5,002,562 | 3/1991 | Oberlander | 606/221 |
| 5,062,848 | 11/1991 | Frazee et al. | 606/219 |

Primary Examiner—Gary Jackson
Attorney, Agent, or Firm—Montgomery W. Smith; Charles F. Costello, Jr.; Rita D. Vacca

[57]        ABSTRACT

A surgical fastener is comprised of a center span with two locking arms extending therefrom, each locking arm containing an indentation adapted to receive a locking point and an indentation adapted to receive a locking nub. An inner bendable member extends from the center span terminating in a staple point member, the staple point member terminating in a tissue piercing point. An outer bendable member extends from the staple point member parallel to the inner bendable member, terminating in a locking point and locking nub. In the closed position the locking point of the outer bendable member locks into the indentation in the locking arm, to lock the staple in the closed position. In the open position the locking nub of the outer bendable member locks into the locking nub indentation in the locking arm to hold the staple in the open position.

3 Claims, 8 Drawing Sheets

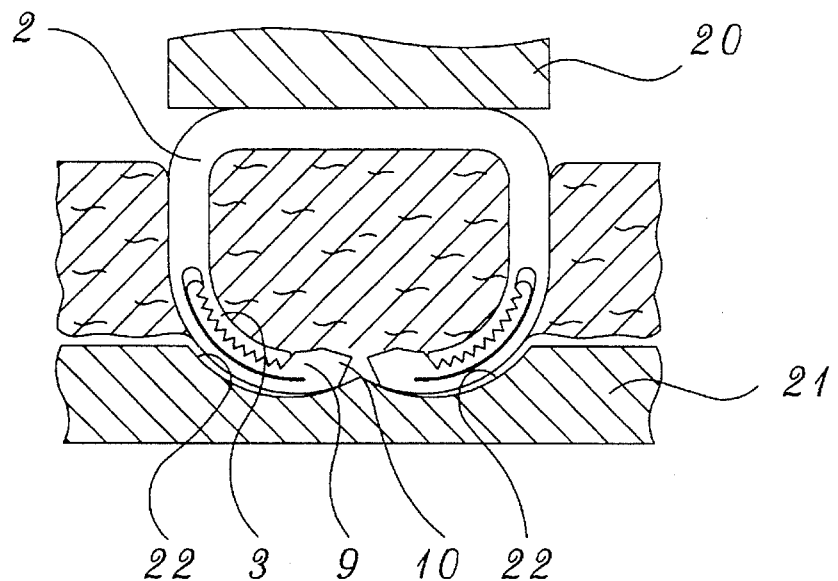
Figure 13
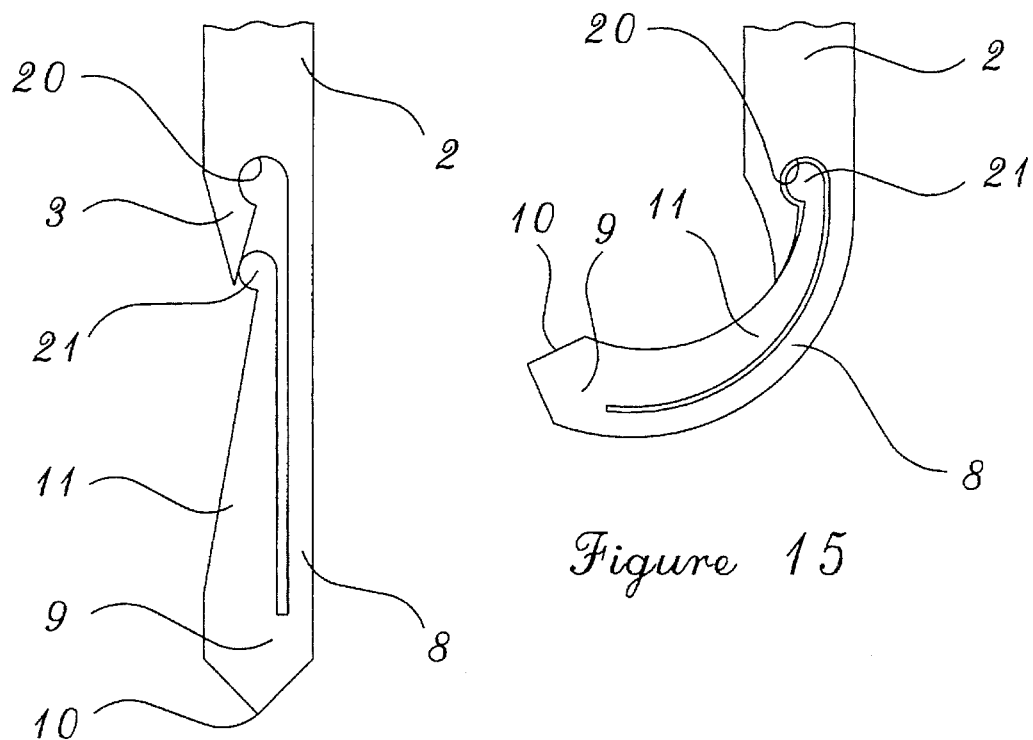
Figure 15
Figure 14

5,540,716

SURGICAL FASTENER

BACKGROUND OF THE INVENTION

This is a continuation of application Ser. No. 08/107,880 filed on Aug. 17, 1993, abandoned, which is a continuation of Ser. No. 07/868,155 filed Apr. 14, 1992, now U.S. Pat. No. 5,236,440.

This invention relates to a surgical fastener, and more particularly to a one part plastic fastener.

Surgical fasteners, or staples, are commonly used in surgical procedures to allow the surgeon to fasten body tissue quickly without the need for time consuming suturing. Such surgical fasteners may be applied by surgical staplers singly, in succession, or a number may be applied simultaneously.

Some types of surgical fasteners are one part devices. That is, they are composed of one piece which interlocks with itself in some manner to form a staple in the closed or locked position.

U.S. Pat. No. 2,881,762 discloses a surgical staple that has two ends. The ends pierce the tissue, overlap and lock. The tissue within the enclosed ring is held together.

U.S. Pat. No. 4,317,451 discloses a one-piece, self-locking, molded plastic staple that has opposed, pointed, L-shaped legs secured to a bridging member. Each leg has an extension, which is engaged by a locking bar when the staple is closed by forcing the legs through a 90° arc.

U.S. Pat. No. 4,428,376 discloses a one-piece, self-locking plastic staple that has an L-shaped leg hinged to a horizontal bridging member. The staple is locked by rotating the leg members 90 degrees as cans engage to hold the legs in place.

U.S. Pat. No. 5,002,562 discloses a surgical clip with a pair of opposed legs formed of rigid biodegradable material. The legs have barbs to hold them in tissue and are connected by a flexible section which is also bioabsorbable. All of the above disclosed patents are incorporated by reference.

One piece staples of the current art are often bulky and, due to the configuration of the staple, are overstressed in the closed position leading to premature failure of the staple when placed in tissue.

It is an objective of this invention to provide a surgical staple which is not bulky in nature, does not put undue stress on the plastic material when the staple is activated, and that holds tissue together for the required period of time to affect healing before losing strength, fracturing, and being bioabsorbed.

It is a further objective of this invention to provide a staple which can be applied from one surface of the tissue only, not requiring an anvil under the tissue to bend the staples. It is also an objective of this invention to provide a staple which can be applied through tissue utilizing an anvil under the tissue.

SUMMARY OF THE INVENTION

A one-piece, self-locking, molded plastic staple is provided which, in the closed configuration comprises a center span with two locking arms extending therefrom, the locking arms containing indentations to receive a point and locking nub, inner bendable members extending from the center span to the staple point, an outer bendable member extending from the staple point back to the locking arms, terminating in a point which is received by the receiving point indentation.

The staple, preferably fabricated in the closed position, is moved to the open position to be ready for use. To open the staple from the closed position, the locking arms are lifted up and the free end of the outer bendable member is brought up under the locking arm where the locking nub on the outer bendable member locks into its mating depression on the locking arm. The staple is then locked in its open position. The staple is fired using an anvil and die mechanism. The anvil is placed under the staple and the die pushes down on the outer bendable members, which bends the member and pulls its end out of the locking nub depression. Further actuation of the die forces the staple into tissue and the free end of the outer bendable member comes out from under the locking arm, and is locked in place by its point fitting into the mating recess in the end of the locking arm.

The inventions can be summarized in the following embodiments:

1. A surgical fastener comprising:

a center span, two locking arms extending from the center span, two inner bendable members extending from the center span and each having a staple point member, the staple point member terminating in a tissue piercing point, two outer bendable members each extending from the respective staple point member and being parallel to the respective inner bendable member, and first means for holding the proximal end of the outer bendable member between the respective inner bendable member and locking arm in an open position, and second means for holding the end of the outer bendable member distal from the juncture of the respective locking arm and said center span in a closed position.

2. A surgical fastener comprising:

a center span, two locking arms extending from the center span, the two locking arms containing indentations adapted to respectively receive an outer bendable member locking point and nub, two inner bendable members extending from the center span and each having a staple point member, the staple point member terminating in a tissue piercing point, and two outer bendable members each extending from the respective staple point member and terminating in a locking point and locking nub.

3. The fastener of embodiment 2 wherein in the open position each locking nub of said two outer bendable members lock into the locking nub indentation in said respective locking arm to hold the staple in the open position, and in said surgical fastener closed position each locking point of the two outer bendable members lock into the locking point indentation in the respective locking arm to lock the staple in the closed position.

4. A surgical fastener comprising:

a center span, two locking arms extending from the center span, the two locking arms each having ratchet teeth on their lower surface, two inner bendable members extending from the center span and each having a staple point member, the staple point member terminating in a tissue piercing point, and two outer bendable members each extending from the respective staple point member and toward the center span, the two outer bendable members each having an end portion, the end portion comprising an upper surface and ratchet teeth on the upper surface to mate with the respective ratchet teeth of said two locking arms.

5. The fastener of embodiment 4 wherein in the open position the end portion of the respective outer bendable member between the respective inner bendable member and said ratchet teeth of said two locking arms is proximal to the juncture of the locking arm and the center span, and in the closed position said end portion of said respective outer bendable member between said respective inner bendable member and said ratchet teeth of said two locking arms is distal to the juncture of the locking arm and the center span.

6. A surgical fastener comprising:

a U-shaped center span, two locking arms extending from the center span, the two locking arms each having ratchet teeth on a surface to mate with an inner bendable member, two outer bendable members extending from the U-shaped center span and terminating in a point member having a pointed end, two inner bendable members each extending from the respective point member toward the U-shaped center span and parallel to the two outer bendable members, the two inner bendable members each having ratchet teeth on a surface to mate with each of said two locking arms.

7. The fastener of embodiment 6 wherein said fastener is closed by use of a pusher and forming die such that the point member is urged in an arc and said two inner and outer bendable members bend, the surface of each of said inner bendable members ratcheting over the ratchet teeth on said two locking arms to lock the staple in the closed position.

8. A surgical fastener comprising:

a U-shaped center span, two locking arms extending from the center span, each having a locking nub indentation;

two outer bendable members extending from the center span and terminating in a point member with a point, and two inner bendable members extending from the point member and parallel to the two outer bendable members, each of the two inner bendable members having a locking nub on their end, the locking nub sliding towards and locking with the locking nub indentation when the staple is closed.

9. The fastener as in any one of embodiments 1 to 8 useful as a surgical staple.

10. The fastener of embodiment 9 having a rectangular cross section.

11. The fastener of embodiment 10 wherein each of said staple point members have a circular cross section.

12. The fastener of embodiment 9 manufactured from a synthetic absorbable polymer.

13. The fastener of embodiment 12 wherein the synthetic absorbable polymer is selected from the group consisting of a homopolymer or copolymer of p-dioxanone, glycolide, lactide and trimethylene carbonate.

14. The fastener of embodiment 9 manufactured from a nonabsorbable polymer.

15. The fastener of embodiment 14 wherein the nonabsorbable polymer is selected from the group consisting of nylon, polyester, polyethylene, polypropylene, and polysulfone.

16. The fastener of embodiment 2 or 3 wherein each of said two locking arms are deflected by said respective inner bendable member as the staple is closed, and the respective end of said inner bendable member is engaged by the respective end of said two locking arms in the fully closed position.

DESCRIPTION OF THE DRAWINGS

FIG. 13 is similar to FIG. 12 showing the staple completely formed and closing the wound.

FIG. 14 is an alternative embodiment of the leg of FIG. 11 in the open position.

FIG. 15 is the leg of FIG. 14 in the closed position.

DESCRIPTION

Figure 1:
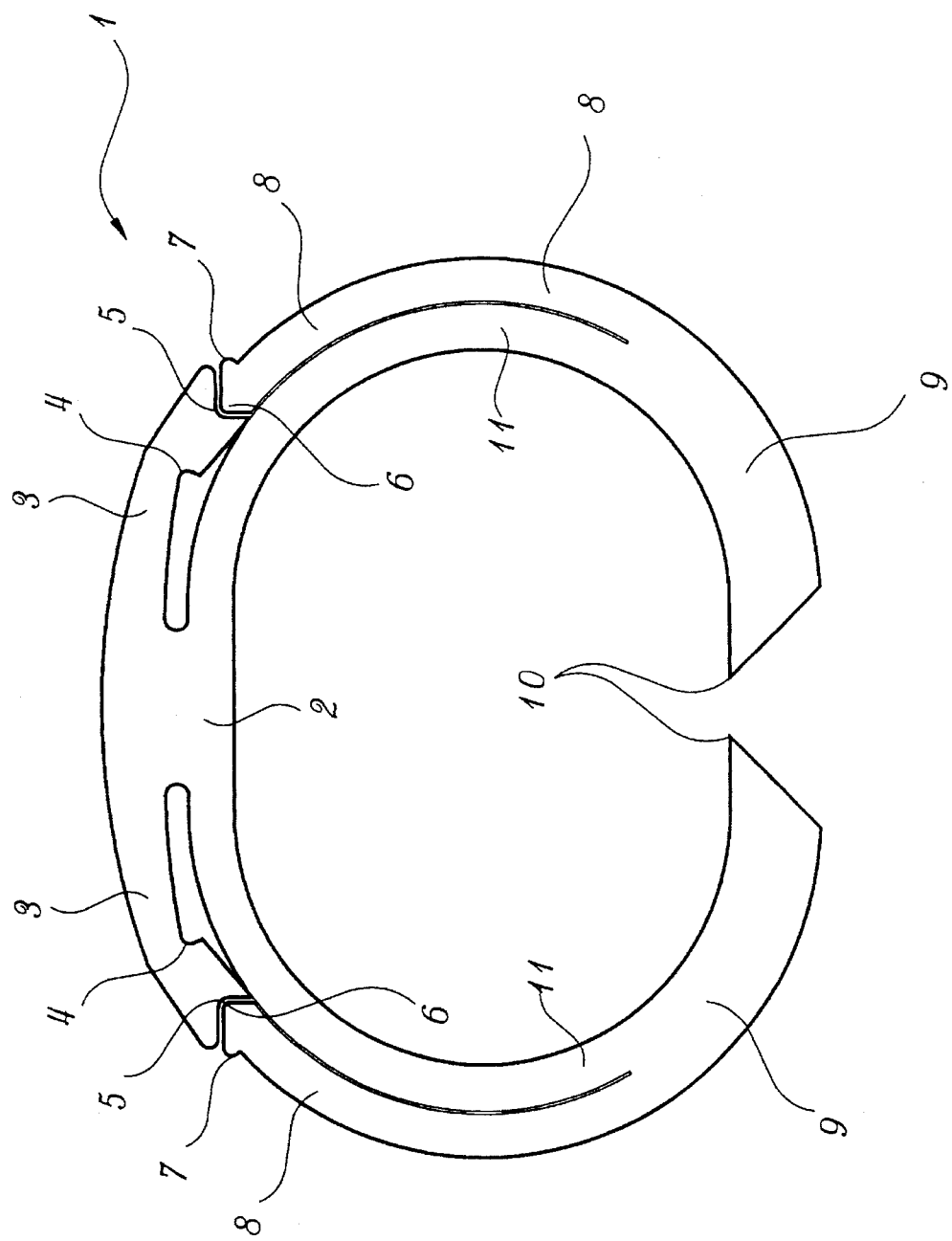
FIG. 1 is an elevational view of a surgical staple according to the present invention in the closed position.
Figure 2:
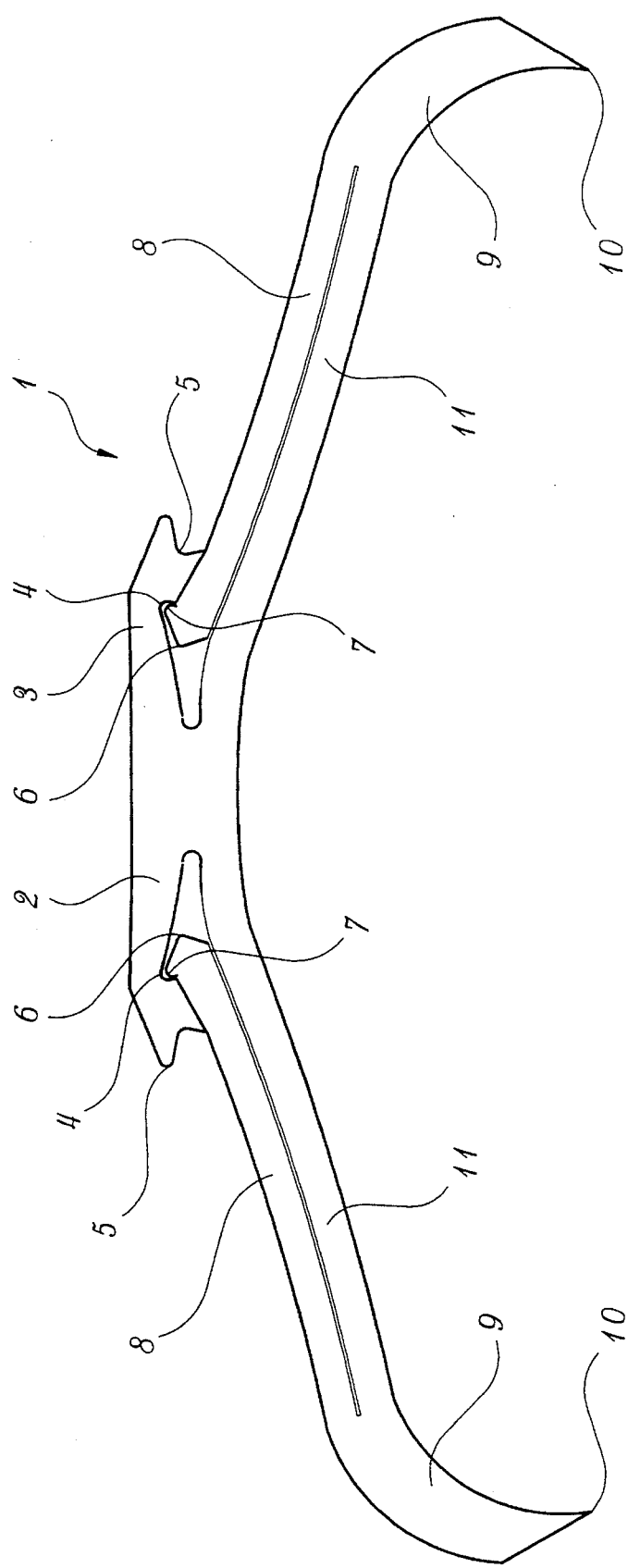
FIG. 2 is an elevation view of the staple of FIG. 1 in the open position.

With reference to FIGS. 1 and 2, there is illustrated staple 1 of the present invention having horizontal bridging member 2 from which extends a locking arm 3 and an inner bendable member 11. The locking arm contains a locking nub indentation 4 and a locking point indentation 5. The inner bendable member connects to the staple point member 9. The staple point member has a point 10 at its end opposite its attachment to the inner bendable member. An outer bendable member 8 is attached to the same end of the staple point member as the inner bendable member, and is parallel to the inner bendable member. The outer bendable member terminates in a locking point 6 and locking nub 7.

Figure 3:
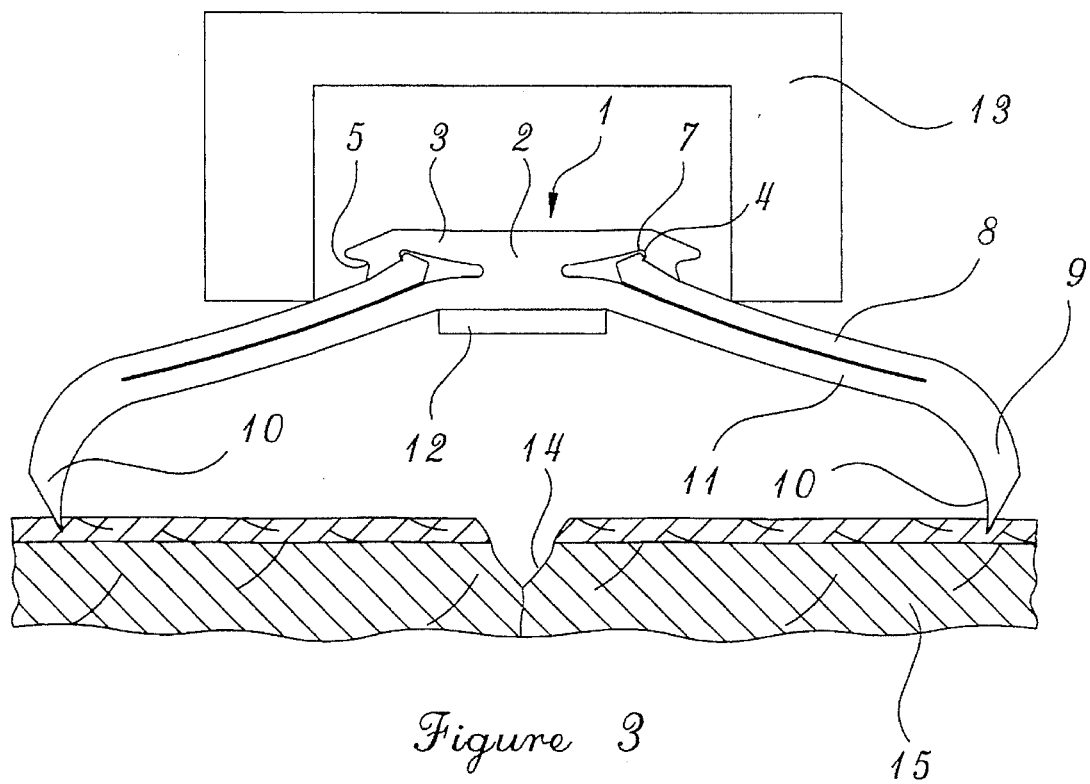
FIG. 3 is a view showing the staple of FIG. 1 in its relationship to the forming anvil, the forming die and the wound which is to be closed.
Figure 4:
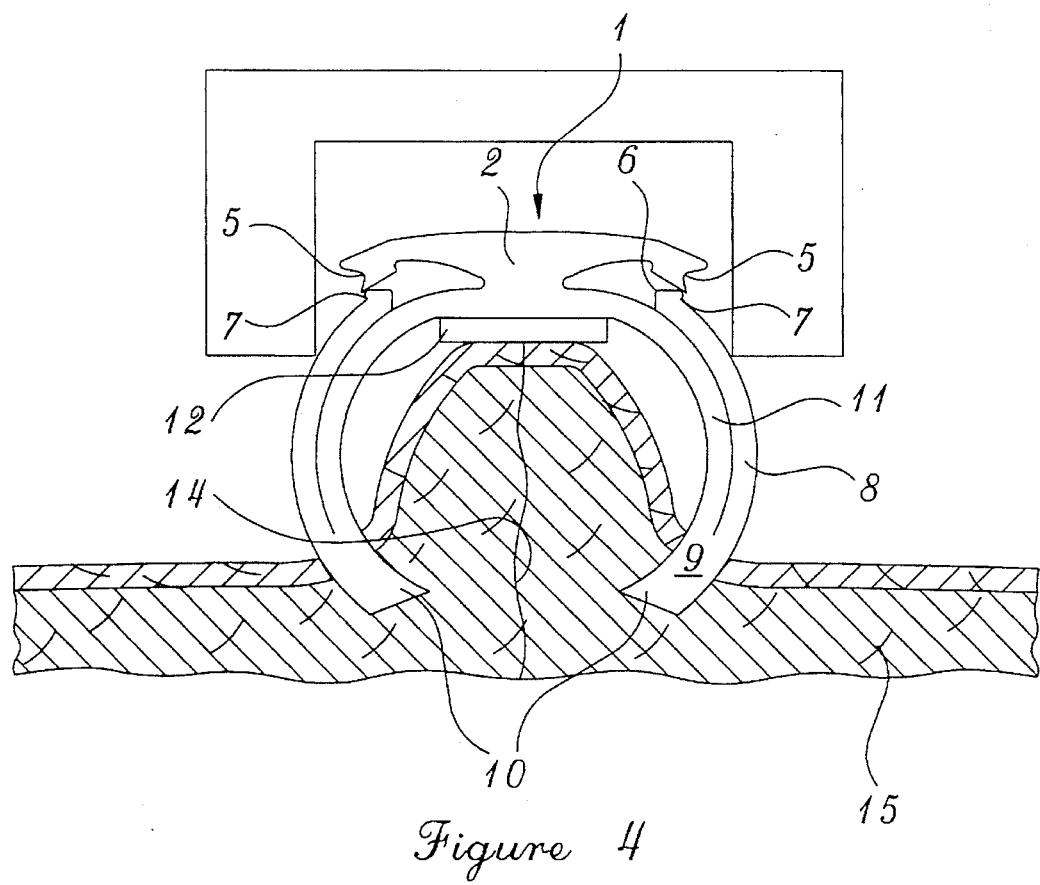
FIG. 4 is a view similar to FIG. 3 showing the staple in the process of being formed.
Figure 5:
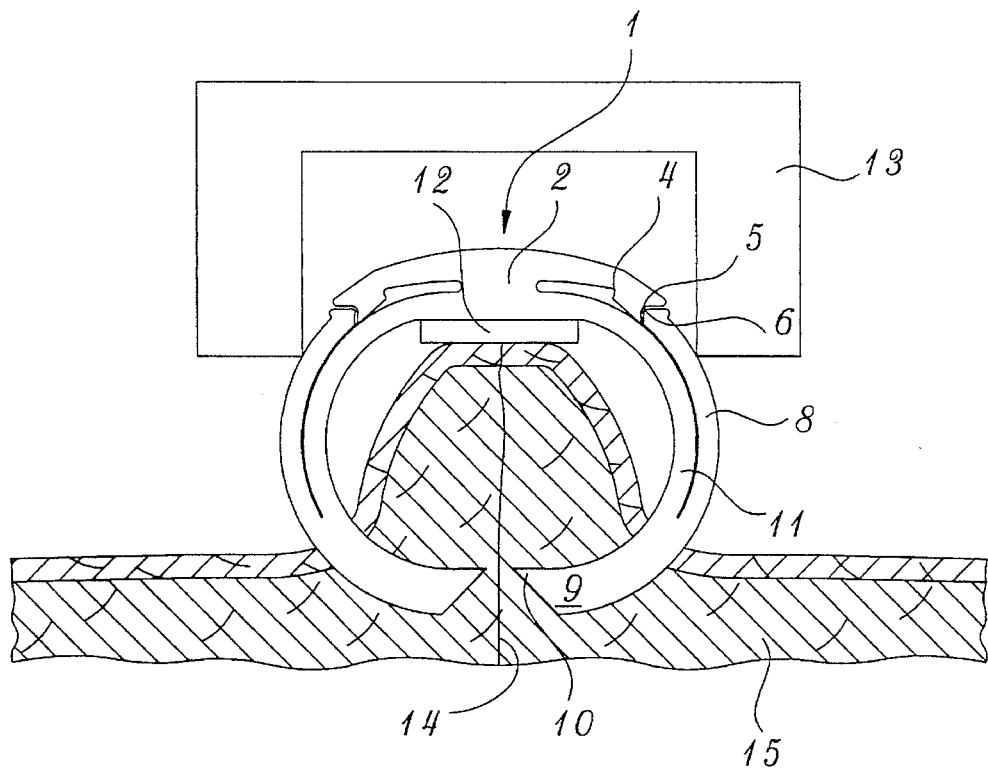
FIG. 5 is a view similar to FIG. 4 showing the staple completely formed and closing the wound.

FIGS. 3 to 6 show the approximation of severed tissue by using staple 1. FIGS. 3 to 5 show the closing of the staple 1 by a device known in the prior art. The device comprises an anvil 12 and a forming blade 13.

As specifically shown in FIG. 3, the staple 1 is held in the closing device by means known in the prior art. The bridging member 2 is supported by the anvil 12. The forming blade 13 abuts the outer bendable member 8. To approximate tissue, the staple closing device and the staple 1 are positioned adjacent to the wound 14. The staple point member extends below the level of the anvil and the staple points initially contact the tissue 15 as the closing device is placed adjacent to the wound 14. As shown in FIGS. 4 and 5, the forming blade 13 is lowered relative to the anvil 12. The staple 1 is thus closed and the wound 14 is approximated. As specifically shown in FIG. 4, during staple closing the staple point members 9 describe an arc causing the outer and inner bendable members to bend around and gather the tissue 15. Upon initial bending of the bendable members the locking nub 7 on the outer bendable member 8 pulls out of the locking nub indentation 4 on the locking arm 3. The locking arm 3 deflects upward to permit the movement of the locking nub 7.

Figure 6:
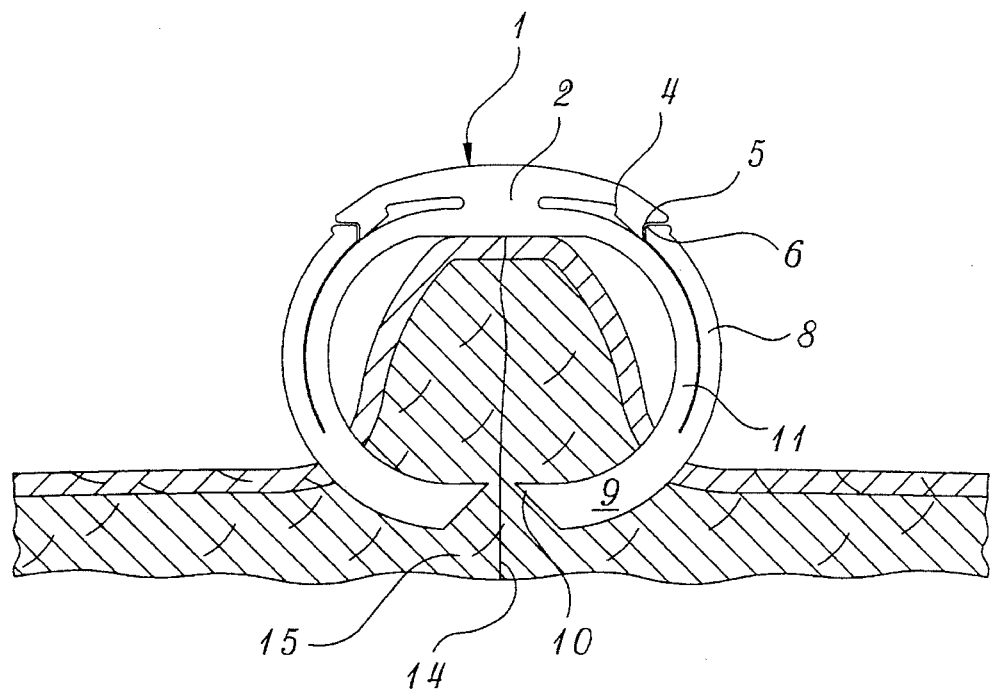
FIG. 6 is a view similar to FIG. 5 showing the wound after the forming tool has been removed.
Figure 7:
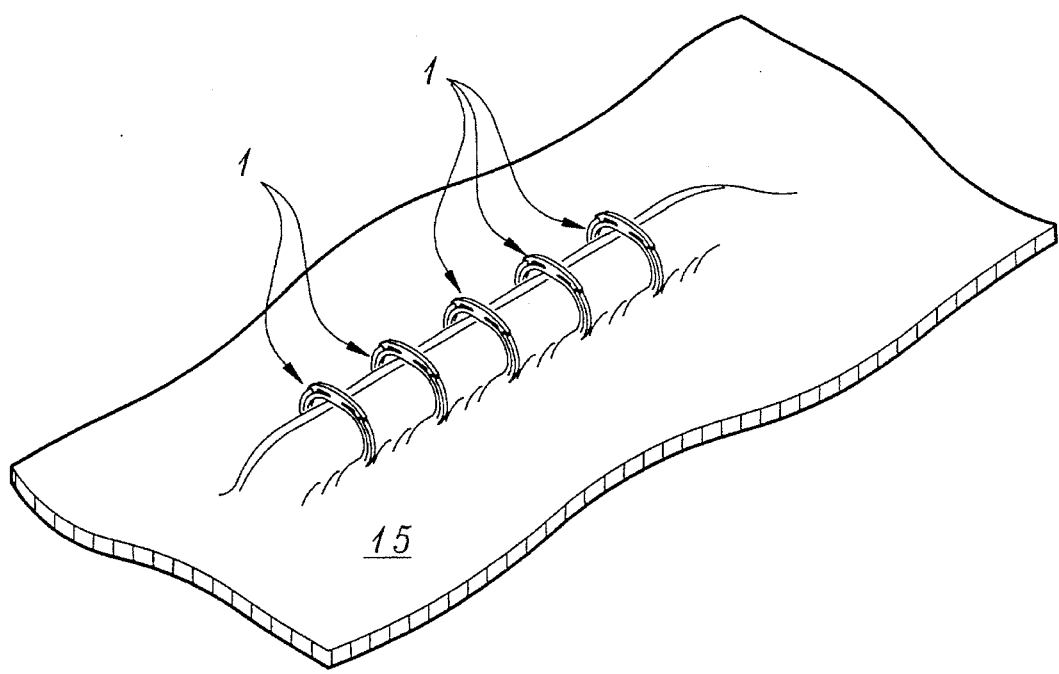
FIG. 7 is a perspective view of a wound properly closed by a plurality of staples according to the invention.

As shown in FIG. 5, the forming blade 13 has completed its compression, and the inner and outer bendable members are in their completely closed position. The locking point 6 bypasses the end of the locking arm 3, and springs up into the locking point indentation in the locking arm. This locks the staple in the closed position. The forming blade 13 is then raised and the closing device is removed from the staple and wound 15. The edges of the wound 14 are approximated for proper healing as illustrated in FIG. 6. FIG. 7 shows a series of staples 1 for closing a wound.

Preferably, the staples of this invention have a rectangular cross section. For ease of penetration in tissue, the staple point member 9 and staple point 10 can be circular in cross section and/or tapered.

Figure 8:
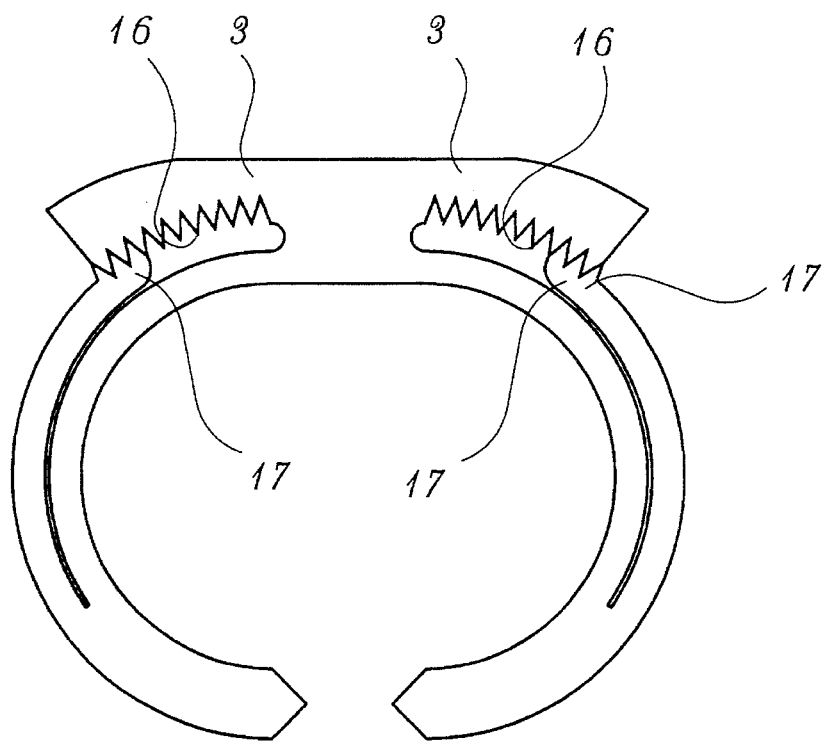
FIG. 8 is an elevational view of another embodiment of a surgical staple according to the present invention.
Figure 9:
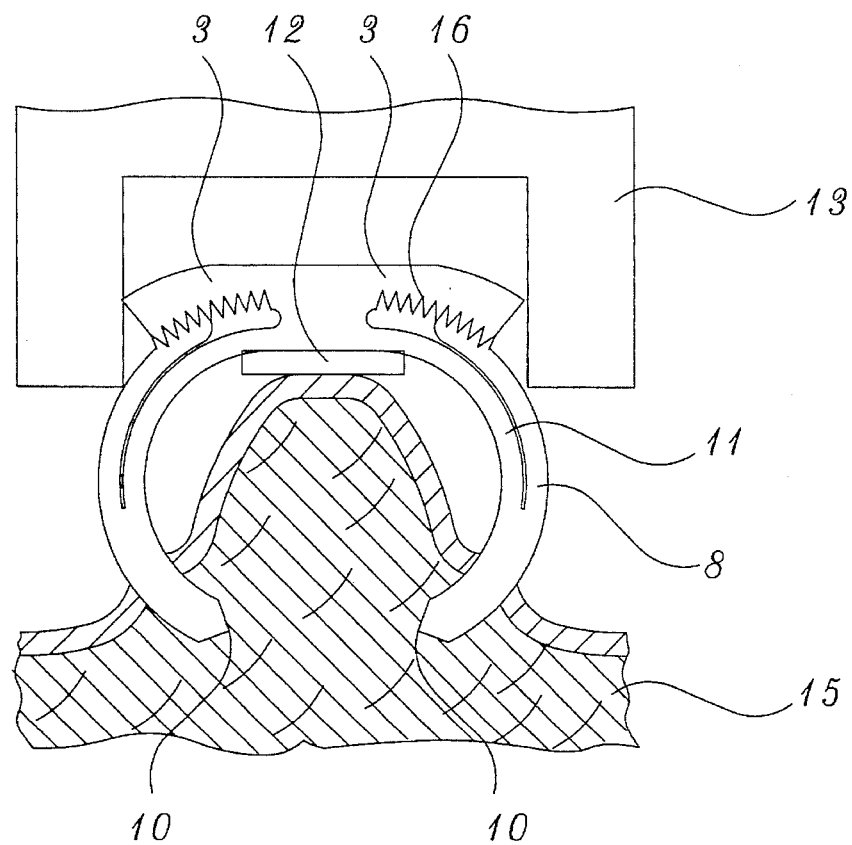
FIG. 9 is a view of the staple of FIG. 8 in a partially closed configuration.

FIGS. 8 and 9 show an alternative embodiment to the staple shown in FIG. 1. The outer bendable member 8 comprises a plurality of ratchet teeth 17 on the upper surface thereof. To engage the ratchet teeth 17 as the staple is closed, locking arm 3 is provided with a mating ratchet surface 16 on the lower surface thereof. The staples shown in FIGS. 8 and 9 may have an advantage over the staple shown in FIG. 1 where it is not necessary or advisable to have complete closure. The staple of FIG. 8 is shown in the partially closed position in tissue in FIG. 9. The staple may be left in the partially closed position by removing the applier if desired, or it can be completely closed.

The staple of the current invention may be used for closing skin, fascia, or internal organs. The staple of this invention can be used with various surgical staplers known in the prior art. For example, the staples can be loaded into a cartridge for use in automatic and/or multiple fired stapling instruments. The instruments can place a plurality of the staples in a straight line or in a circle pattern. The modification, if any, of the prior art stapling instruments can be conducted by any person skilled in the art without undue experimentation.

FIGS. 10 to 13 show another embodiment of the current invention adapted to staple through tissue and have a forming die on the opposite side of the tissue for forming the staple. This is the type of staple currently used in linear or circular internal staplers.

Figure 10:
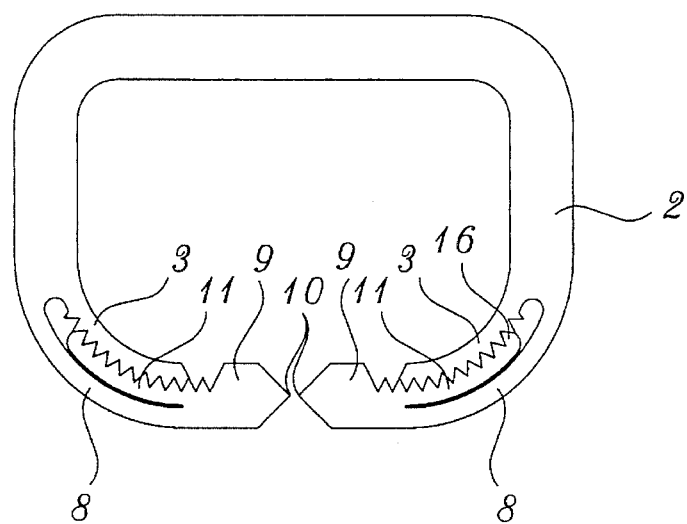
FIG. 10 is an elevational view of another embodiment of a surgical staple according to the present invention in the closed position.
Figure 11:
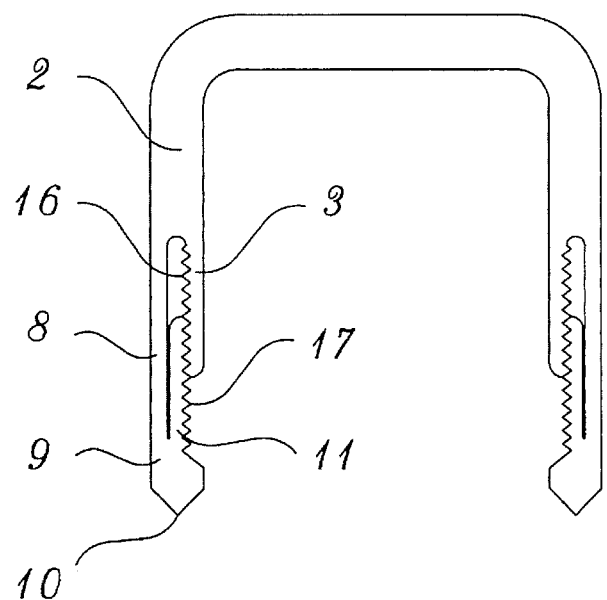
FIG. 11 is a view of the staple of FIG. 10 in the open position.
Figure 12:
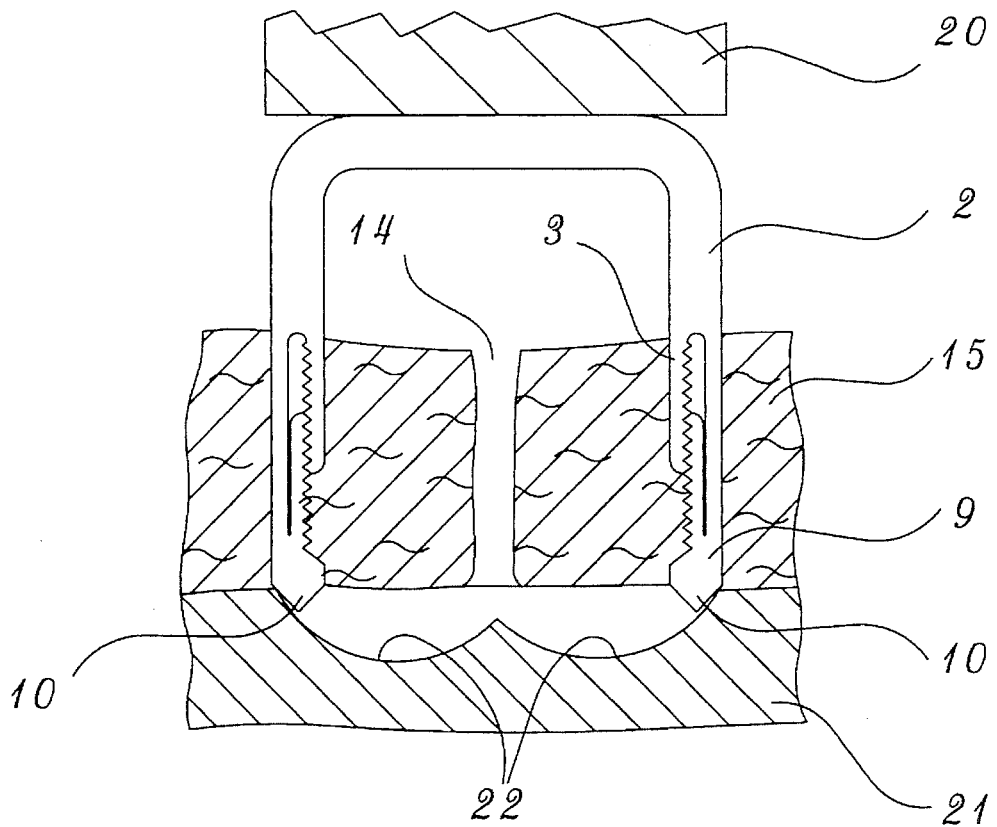
FIG. 12 is a view of the staple of FIG. 11 in its relationship to the forming anvil, the forming die and the wound which is to be closed, in the open position.

With reference to FIG. 10, U-shaped bridging member 2 terminates on the inside with a locking arm 3, which has ratchet receiving serrations 16 on its surface, and terminates on the outside with an outer bendable member 8 which joins point member 9. The point member has a point 10 at its tip and an inner bendable member 11 which extends from the point member 9 in a direction parallel to the outer bendable member 8. The inner bendable member 11 has a ratcheting surface 17 which mates with the ratchet receiving serrations 16 on the locking arm. In FIG. 10 the staple is shown locked in the closed position, with the ratchet surface 17 engaging the ratchet receiving serrations 16. FIG. 11 shows the staple in the open position. FIG. 12 shows the staple being applied to tissue. The staple point members 9 have penetrated the tissue 15 on both sides of the wound 14, pushed by the pusher 20. The staple tip 10 is contacting the anvil forming grooves 22 which will urge the bendable members to bend into their closed position with further advancing of the pusher 20. FIG. 13 shows the staple in its fully closed position, where the anvil forming grooves have bent the bendable members and forced the inner bendable member to advance toward the U-shaped bridging member causing its ratchet surface to engage and lock with the ratchet receiving serrations on the locking arm, holding the staple in its closed position.

FIGS. 14 and 15 show another embodiment of the current invention for the staple type of FIG. 10. Only the working member is shown in its open and closed position. With reference to FIG. 14, U-shaped bridging member 2 terminates on the inside with a locking arm 3, which contains a locking nub receiving indentation 20, and terminates on the outside with an outer bendable member 8 which joins point member 9. The point member has a point 10 at its tip and an inner bendable member 11 which extends from the point member 9 in a direction parallel to the outer bendable member 8. The inner bendable member has a locking nub 21 on its end that mates with the locking nub receiving indentation 20 in the closed position. In FIG. 15 the staple leg is shown in its closed position with the locking nub 21 resting in the locking nub indentation 20. FIGS. 14 and 15 show only one working member of a staple, which would have two locking members and a U-shaped bridging member.

The staples of this invention can be manufactured in sizes similar or identical to prior art metallic staples. As an average, the bridging member can be from about 0.2 to 0.6 cm. The inner and outer bendable members can then be sized proportionally, e.g. as shown in FIG. 1. The manufacture of the staple of this invention can be by any suitable plastic forming technique, e.g. extrusion and injection molding. Any known biocompatible material may be useful, although several known synthetic polymeric compositions are also bioabsorbable and are therefore preferred. Nonabsorbable polymeric compositions include, but are not limited to, nylon, polypropylene, polyester, and polysulfone.

Examples of bioabsorbable polymers include, but are not limited to, homopolymers and copolymers of lactide, glycolide, trimethylene carbonate, and p-dioxanone.

Where absorption is not important and/or critical, e.g. in some internal surgical procedures, nonabsorbable staples of polypropylene or nylon may be useful. Referring to FIGS. 6 and 9 for external uses, the staple is relatively easily removed after the wound has sufficiently healed by raising the bridging member 2 or locking arms 3, respectively. The staple can then be removed by rotating the bendable members back to their original open position as illustrated in FIG. 2.

It is to be understood that other embodiments not specifically described above are within the scope of this invention.

I claim:

1. A surgical fastener comprising at least two inner bendable members each having a first and second end, at least two locking arms each having a first and second end, and at least two outer members each having a first and second end, the first end of each of said locking arms and said outer members being attached respectively to the first and second end of each of said inner bendable members; and the second end of each of said locking arms and said outer members including means for holding the second end of each of said locking arms and said outer members in at least two different positions relative to each other.

2. A surgical fastener consisting essentially of two locking arms each having a first and second end, two outer members each having a first and second end, and two inner bendable members extending from the first end of each of said two locking arms to the first end of each of said outer members; and the second end of each of said two locking arms and said two outer members including means for holding the second end of each of said two locking arms and said two outer members in at least two different positions relative to each other.

3. A surgical fastener comprising at least two outer bendable members, at least two locking arms and at least two inner members, each of said outer bendable members, said locking arms and said inner members having a first end second end; the first end of each of said locking arms and said inner members being attached to the first and second end respectively of each of said outer bendable members, and the second end of each of said locking arms and said inner members including means for holding the second end of each of said locking arms and said inner members in at least two different positions reactive to each other.

* * * * *

UNITED STATES PATENT AND TRADEMARK OFFICE
CERTIFICATE OF CORRECTION

PATENT NO. : 5,540,716

DATED : July 30, 1996

INVENTOR(S) : Robert A. Hlavacek

It is certified that error appears in the above-identified patent and that said Letters Patent are hereby corrected as shown below:

On the Title page, item [75]: Inventor's city address;

please delete "Navgetuck" and insert -- Naugatuck --.

In Column 1, line 34, delete "cans" and insert - cams -.

In Column 8, at the end of line 4, after "first end", insert - and a -.

In Column 8, last line, delete "reactive" and insert - relative -.

Signed and Sealed this

Fifteenth Day of April, 1997

*Attest:*

BRUCE LEHMAN

*Attesting Officer*      *Commissioner of Patents and Trademarks*